(12) United States Patent
Hara et al.

(10) Patent No.: US 7,753,525 B2
(45) Date of Patent: Jul. 13, 2010

(54) OPHTHALMIC APPARATUS

(75) Inventors: Takuya Hara, Hamamatsu (JP); Satoshi Shimada, Hamamatsu (JP)

(73) Assignee: Kowa Company, Ltd. (JP)

( * ) Notice: Subject to any disclaimer, the term of this patent is extended or adjusted under 35 U.S.C. 154(b) by 0 days.

(21) Appl. No.: 12/269,242

(22) Filed: Nov. 12, 2008

(65) Prior Publication Data
US 2009/0122263 A1 May 14, 2009

(30) Foreign Application Priority Data
Nov. 12, 2007 (JP) .............................. 2007-292862
Dec. 5, 2007 (JP) .............................. 2007-314433

(51) Int. Cl.
*A61B 3/02* (2006.01)
(52) U.S. Cl. ........................ 351/226; 351/224; 351/223
(58) Field of Classification Search ................. 351/224, 351/226, 200, 222, 225, 237, 239, 223
See application file for complete search history.

(56) References Cited
U.S. PATENT DOCUMENTS
5,459,536 A 10/1995 Shalon et al.

FOREIGN PATENT DOCUMENTS
| EP | 1 366 706 | 12/2003 |
|----|-----------|---------|
| EP | 1 520 510 | 4/2005 |
| WO | WO/99/21474 | 5/1999 |

OTHER PUBLICATIONS
European Search Report, Mar. 30, 2009, European Patent Office.

*Primary Examiner*—Jack Dinh
(74) *Attorney, Agent, or Firm*—Law Offices of Robert F. Zielinski, LLC

(57) ABSTRACT

A virtual sensitivity value which is obtained, variously changing a pupil diameter is measured in advance for many examinees, and volume of correction which is necessary at the time when the sensitivity value is corrected into one in a standard pupil diameter is stored as correction volume database. An apparatus has measurement means for measuring the pupil diameter of the eye to be examined, computing means for computing a shape parameter rate of the measured pupil diameter to the standard pupil diameter, and judgment means for computing volume of correction by referring to the correction volume database from the shape parameter rate and correcting the virtual sensitivity value obtained by measurement of the eye to be examined and for judging a sensitivity step of the eye to be examined.

3 Claims, 5 Drawing Sheets

FIG.4

TBL1

| p VALUE | ... | AGE 10 | AGE 11 | AGE 12 | ... | AGE 87 | AGE 88 | AGE 89 | ... |
|---|---|---|---|---|---|---|---|---|---|
| ≧5% | ... | ... | ... | ... | ... | ... | ... | ... | ... |
| <5% | ... | ... | ... | ... | ... | ... | ... | ... | ... |
| <2% | ... | ... | ... | ... | ... | ... | ... | ... | ... |
| <1% | ... | ... | ... | ... | ... | ... | ... | ... | ... |
| <0.5% | ... | ... | ... | ... | ... | ... | ... | ... | ... |

SNX  SNX  SNX

FIG.5

TBL2

| AGE 10 OR YOUNGER | 20S | ... | 60S | 70S |
|---|---|---|---|---|
| $y=f_{10}(n)$ | $y=f_{20}(n)$ | ... | $y=f_{60}(n)$ | $y=f_{70}(n)$ |

OPHTHALMIC APPARATUS

CROSS-REFERENCE TO RELATED PATENT APPLICATIONS

This application claims priority under 35 U.S.C. §119(a) to Japanese Patent Application Nos. 2007-292862, filed Nov. 12, 2007 and 2007-314433, filed Dec. 5, 2007, the entireties of which are hereby incorporated by reference.

BACKGROUND OF THE INVENTION

This invention relates to an ophthalmic apparatus for measuring a response state to light stimulus given to an eye to be examined.

BACKGROUND ART

Some of ophthalmic apparatuses examine a visual function by receiving a response (reaction) from an examinee when perceiving a light stimulus by himself (herself) or confirming the perception by the examinee with another means. A perimeter and an ERG are their typical examples.

An eye of a person has a pupil, and the pupil has a function of adjusting an incident light in such a manner that it contracts for limiting entered energy at the time when an eye receives a strong incident light, and expands for obtaining more energy as the entered energy becomes low.

In the ophthalmic apparatus for photographing fundus image, such a technique is known that a size of a pupil, that is, a pupil diameter is measured, and a gain of photographic means is adjusted by the pupil diameter so as to obtain a good image (see Japanese patent application publication No. 2005-87300).

"The ophthalmic apparatus for examining a visual function by receiving a response (reaction) from an examinee when perceiving a light stimulus by himself (herself) or confirming the perception by the examinee with another means" which was above-mentioned as an example outputs a response state of the eye to be examined to predetermined volume of light energy which is outputted by the apparatus as measurement results. However, energy which actually enters the eye to be examined is different in each examinee due to a different pupil area in the respective examinees even if the above-mentioned apparatus emits predetermined volume of light energy since energy which actually enters the eye to be examined is only one after passing the pupil. Then, a luminance on a retina of the eye to be examined changes, and volume of radiated light energy is different from volume of light energy to which the eye to be examined actually reacts. As the result, the measurement result may be incorrect. Then, some effective measure is desired since the object is to test the response state of the eye to be examined to the entered light energy, and the above-mentioned problem can not be solved by adjusting the gain of the photographic means which is shown in the Japanese patent application publication No. 2005-87300.

If there is no stimulus excluding the stimulus light (that is, if a background light for lighting a whole visual field for measurement is not used), volume to be compensated in connection with a measurement result can be generally obtained only from an area rate between the pupil diameter which is detected from the obtained result and a standard pupil diameter even if the luminance on the retina is changed due to such a change of the pupil diameter.

For example, the rate of the pupil area of the examinee at the time of a measurement to the standard pupil area is two (2) supposing that the standard pupil area is D, the measured pupil area of an examinee A at the time of an examination is 0.5 D, and an amount of stimulus of the examinee A at the time of a response in some point is T. Therefore, it is easily possible to obtain the volume of correction by computing the sensitivity with the volume of stimulus as T/2.

However, a problem may occur if the sensitivity is computed only by the area rate to the standard pupil diameter in a case where the stimulus light having predetermined light energy is emitted under a predetermined background light at the time of a measurement with a general perimeter in order to test a response state of the eye to be examined to the stimulus light since an element, a contrast with the background light is added in addition to the volume of stimulus (luminance on the retina) as an absolute value.

If the volume of stimulus with which the examinee responds is T in a measurement point where the volume of stimulus by the background light is B, the volume of stimulus by the stimulus light is S and the standard pupil area is D, when the measured pupil area of the examinee A at the time of examination is 0.5, the rate of the pupil area of the examinee A at the time of examination to the standard pupil area is 1:2. So, the luminance on the retina of the examinee A is ½. This is because both, the background light and the stimulus light become ½, and the contrast between the background light and the stimulus light does not change, and only volume of light which passes the pupil changes.

In the measurement result in the perimeter, the sensitivity is generally computed by the volume of stimulus on the assumption that the volume of stimulus by the background light is constant. If the sensitivity is computed by only area rate and the volume of stimulus after correction is T/2, both the background light and the stimulus light are doubled. Therefore, the volume of stimulus of the background light is double increased. Then, it is not possible to obtain a correct measurement result since the result is different from a case where the background light is constant and only the stimulus light is doubled in a desired correction. Some effective measure is desired.

Under the above-mentioned circumstances, an object of the invention is to provide an ophthalmic apparatus which can be obtained correct measurement results according to the pupil diameter of the eye to be examined even in a case where the stimulus light having predetermined light energy is emitted under a predetermine background light so as to test the response state of the eye to be examined to the stimulus light.

SUMMARY OF THE INVENTION

One aspect of the invention is an ophthalmic apparatus for computing a sensitivity value of an eye to be examined in a measurement point in such a manner that a stimulus light from a lamp having one, two or more different kinds of strength, is emitted on a retina of said eye to be examined from a predetermined said measurement point as a stimulus under a predetermined background light, and a response of an examinee to said stimulus light is obtained, comprising:

a memory for storing sensitivity database wherein a sensitivity of said eye to be examined in said measurement point which corresponds to said sensitivity value which is obtained with said eye to be examined having a standard pupil diameter when said stimulus light having one, two or more different kinds of strength is used as said stimulus under said predetermined background light is shown in two or more sensitivity steps;

a memory for storing volume of correction which is necessary for correcting a virtual sensitivity value which was measured with said pupil diameter of some shape parameter into a sensitivity value in a standard pupil diameter as a correction database after said virtual sensitivity value which is obtained when measuring said eye to be machined which sensitivity value in said standard pupil diameter is known, variously changing said pupil diameter under said predetermined background light is measured for many examinees in advance;

a pupil diameter measuring unit for measuring a pupil diameter of said eye to be examined;

a shape parameter rate computing unit for computing a shape parameter rate of said measured pupil diameter to said standard pupil diameter;

a correction volume computing unit for computing volume of correction by referring to said correction volume database from said shape parameter rate of said eye to be examined; and a sensitivity step judging unit for judging said sensitivity step of said eye to be examined in such a manner that said virtual sensitivity value which was obtained by a measurement of said eye to be examined is corrected into said sensitivity value in said standard pupil diameter by said computed volume of correction, and said corrected sensitivity value in said standard pupil diameter is referred to as said sensitivity database.

According to this aspect of the invention, it is possible to obtain a correct measurement result according to the pupil diameter of the eye to be examined even if a stimulus light having predetermined light energy is radiated under a constant background light in order to examine a response state of the eye to be examined to the stimulus light since the volume of correction which is necessary for correcting the virtual sensitivity value which was measured with the pupil diameter of some shape parameter rate into the sensitivity value in the standard pupil diameter is obtained from the correcting volume database, and on the basis of the obtained volume of correction, the virtual sensitivity value which was obtained by the measurement of the eye to be examined can be corrected so as to judge the sensitivity stage from the sensitivity database on the basis of the standard pupil diameter.

Besides, other aspect of the invention is the ophthalmic apparatus, wherein said ophthalmic apparatus is a perimeter.

Furthermore, another aspect of the invention is the ophthalmic apparatus, wherein said ophthalmic apparatus is an ERG (Electororetinograph).

BRIEF DESCRIPTION OF THE DRAWINGS

FIG. 4 is a view showing an example of normal sensitivity distribution data by age in each measurement point.

FIG. 5 is a view showing an example of a correction function for obtaining volume of correction to a virtual sensitivity value of the eye to be examined.

BEST MODE FOR CARRYING OUT THE INVENTION

Figure 1:
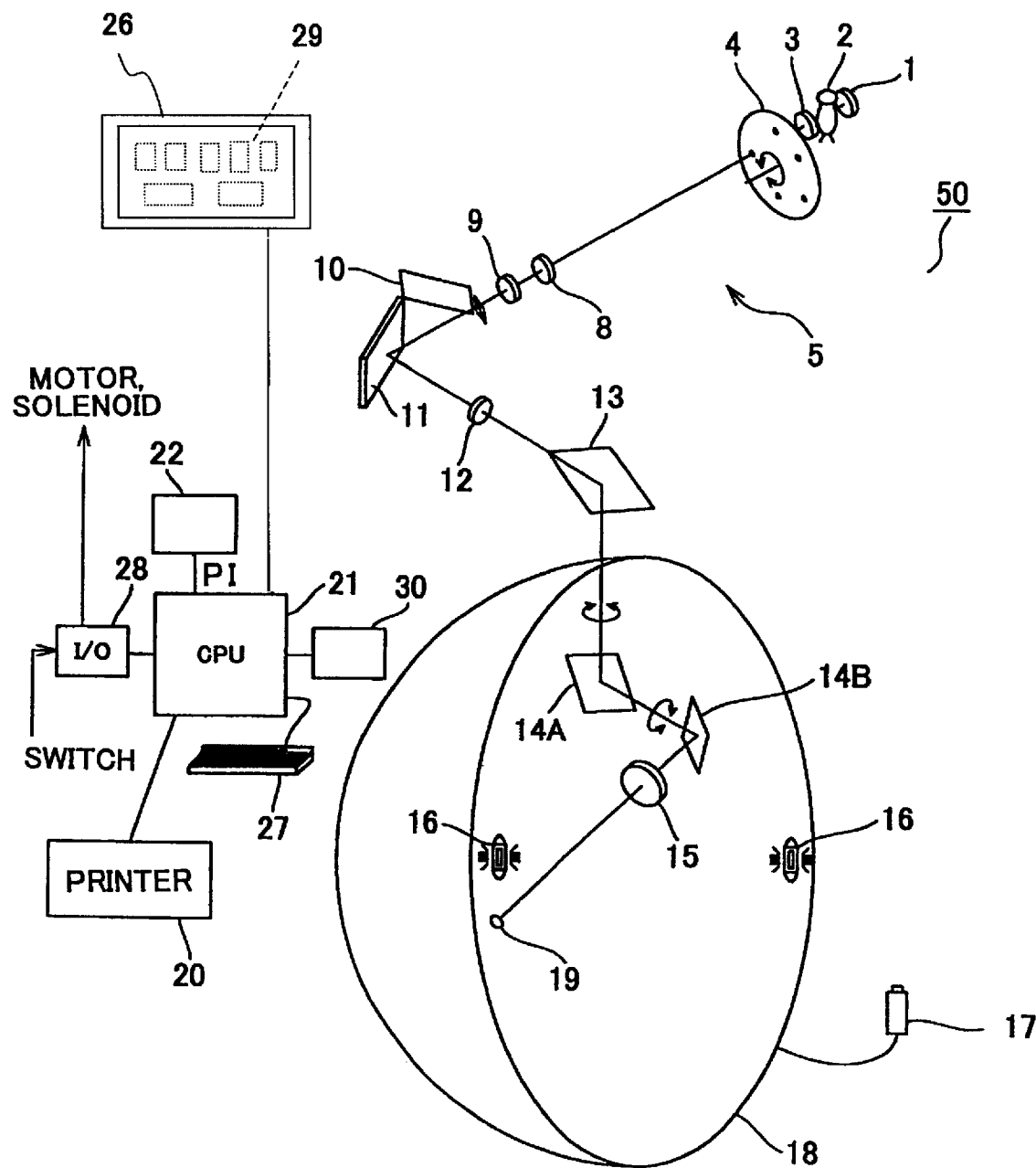
FIG. 1 is a view showing an example of a structure of a perimeter which is one of ophthalmic apparatuses.

As shown in FIG. 1, a perimeter 50 which is one of ophthalmic apparatuses has a visual field dome 18 in the shape of a hemi-sphere, and a chin rest (not shown) for an examinee is located at a central position of the visual field dome 18. When measuring, a position of the chin rest is aligned so as to position an eye to be examined 40 at a center of the visual field dome 18 through an alignment mechanism (not shown). Lamps 16, 16 for background lightning are arranged at two positions inside the visual field dome 18.

The examinee is invited to fixate a stimulus 19 which is lighted with predetermined brightness by background light from the lamps 16, 16 and is projected on a projection plane inside the visual field dome 18, and returns a replay to an examiner by some proper method, such as by operating a response switch 17 or replying with voice when perceiving the stimulus.

In order to project the stimulus 19, a stimulus projection mechanism denoted with a reference numeral 5 is located in FIG. 1. A reference numeral 2 denotes a stimulus projection lamp (halogen lamp) as a light source, and a reflecting mirror 1 is located at the back thereof. Light of the stimulus projection lamp 2 is injected into a relay lens 8 through a condenser lens 3 and an aperture 4. The aperture 4 can determine a size of the stimulus, and has two or more openings so that a proper sized opening can be moved onto an optical axis through a control by a CPU 21 as mentioned hereinafter. Furthermore, the light is reflected by a mirror 11 after passing the relay lens 8, a focus lens 9 and (an opening of) a shutter 10, and is reflected by a mirror 11 and is reflected by a mirror 13 via a relay lens 12. Light emitting diode can be used as the lamp for projecting stimuli in place of a halogen lamp. In such a case, the reflecting mirror is not necessary.

In this embodiment, two mirrors 14A and 14B are provided in order to control a projection position of the stimulus 19, and a swinging position of the mirror is controlled by the CPU 21 through a driving mechanism, such as a motor (not shown). Finally, the stimulus 19 is projected on the projection plane of the visual field dome 18 through a projector lens 15.

The perimeter according to the present embodiment can be used as an automatic perimeter by controlling the stimulus projecting mechanism 5 according to predetermined program by a control by the CPU 21.

Figure 2:
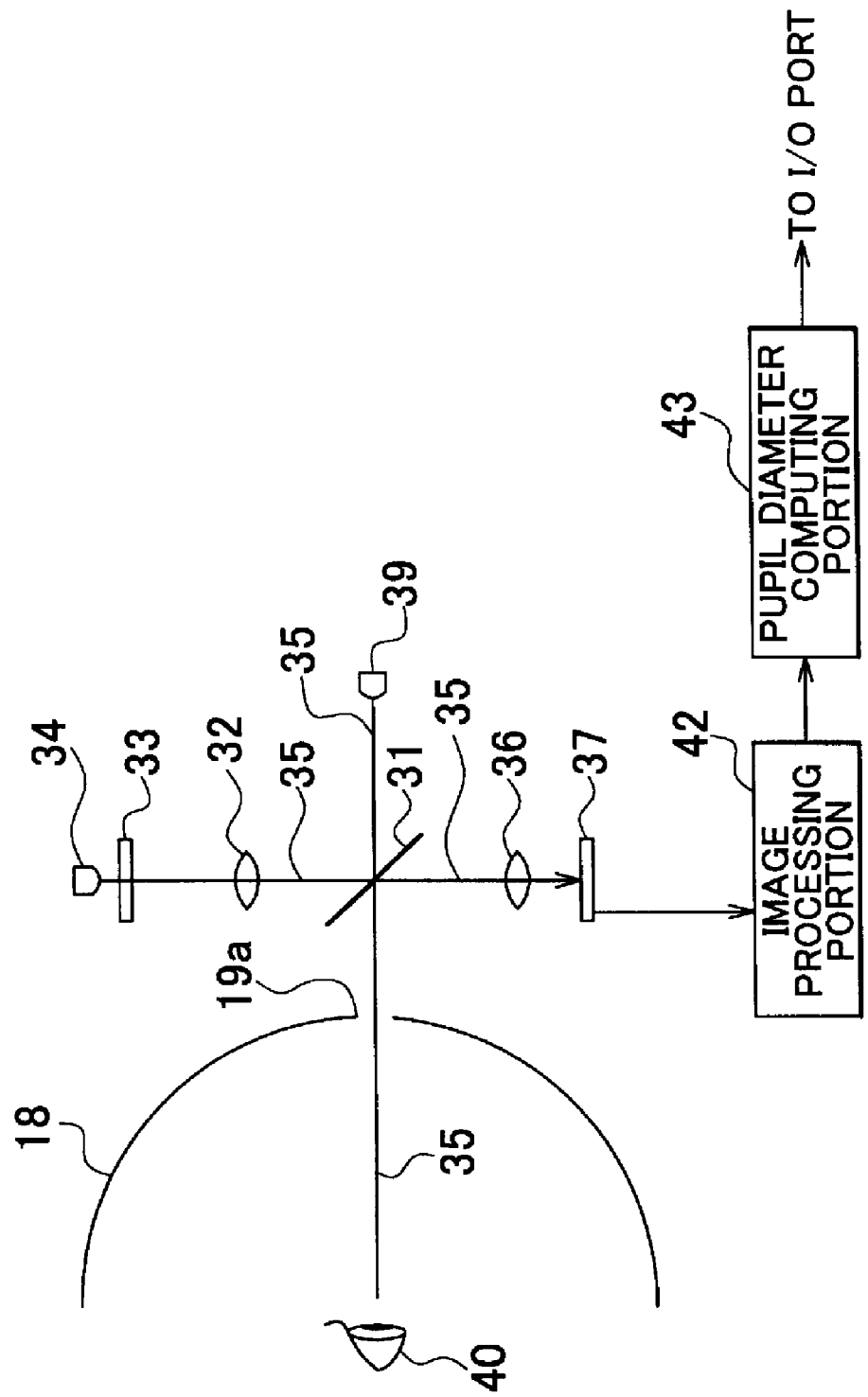
FIG. 2 is a typical view showing details of a pupil diameter to be measured in the perimeter of FIG. 1.

As shown in FIG. 2, a monitor hole 19a is formed at a farthest portion in the right hand portion of the visual field dome 18 in a horizontal direction rather than a central position of the visual field dome 18 which is positioned by the chin stand for the eye to be examined 40, and a beam splitter 31 is provided on the right hand in the figure. On an optical path 35 on the upper hand in the figure with respect to the beam splitter 31, an aperture 33 on which a photographed stimulus is described and a lamp 34 as a light source are provided through one or more lens 32. And, on the optical path 35 on the lower hand in the figure with respect to the beam splitter 31, a CCD camera 37 is provided through an imaging lens 36. On the optical path 35 in the right hand in the figure with respect to the beam splitter 31, a light source for fixation 39 which is comprised of LEDs is provided.

A control system of the perimeter according to this embodiment has the following structure. The CPU 21 controls a motor, a solenoid and the like which are included in the above-mentioned stimulus projecting mechanism (1 through 15) through an I/O port 28, and inputs information from the response switch 17. In addition, the I/O port 28 is connected with the CCD camera 37 through an image processing portion 42 and a pupil diameter computing portion 43.

And, a monitor 26 which is comprised of a display unit, such as a LCD and a CRT, is connected with the CPU 21, and is used for outputting test data or displaying a menu at a time of setting. A touch panel 29 (a method of detecting a coordinate is optional) is located on a screen of the monitor 26, and with this touch panel 29, the menu can be selected and a coordinate of a stimulus projection position can be inputted through a finger or a dedicated input pen.

An examiner can control a perimetry with the touch panel 29 or a keyboard 27. When designating one of perimetry programs and inputting a test start, the position where a stimulus is projected is controlled according to the designated perimetry program, and a response by the response switch 17 is inputted. During the perimetry, data resulting from the perimetry is stored in memories 22, 30 which are respectively comprised of an optional storage device, such as a RAM and a hard disc. In addition, such data is displayed on the monitor 26, is printed out with a printer 20, or is outputted to an outside device as an electronic file, if necessary.

At the time of perimetry, the stimulus which is located on the aperture 4 is projected at a proper position inside the visual field dome 18 by a well-known method. When the examinee who perceived the projected stimulus operates the response switch 17 within a predetermined limited time, the CPU 21 confirms the examinee's perception of the projected stimulus 19. The perimetry is conducted by a well-known method in such a way that the stimulus 19 is projected and presented to an examinee at predetermined time intervals at a lot of measurement points inside the visual field dome 18 in order to confirm in which degree the examinee can perceive the stimulus.

At the time of such a perimetry, the examiner selects and inputs the perimetry which is scheduled to be conducted on the examinee through the keyboard 27 or the touch panel 29. Two or more perimetry methods which can be selected with the perimeter 50 are stored in the memory 22 (or 30) of the perimeter 50 so as to be selected as the perimetry program, and the examiner can select the proper perimetry from two or more perimetry methods which are displayed on the monitor 26.

Perimetry data of an examinee is stored in the memory 22 (or 30) as examinee measurement information PI together with identification information, such as ID number of each examinee. In the examinee measurement information, test points, such as an optic disc of a fundus, macula and nasal of the eye, are set and stored according to a condition, a kind or a proceeding of disease of an examinee. Besides, names, ages and sexes of examinees, test methods at the time of perimetry, test patterns, past measurement results are also stored in the examinee measurement information PI in addition to the above-mentioned data. Then, these data can be read out of a memory on the basis of the ID of each examinee so as to be displayed on the monitor 26 and can be utilized as data to be used for future perimetry.

The perimeter 50 as the ophthalmic apparatus has the above-mentioned structure. In order to conduct a perimetry on the eye to be examined 40, in advance of such perimetry, the eye to be examined 40 is firstly positioned by adjusting the chin stand (not shown) so as to be at a central portion of the visual field dome 18. That is, the examiner operates the tough panel 29 in order to turn on the light source for fixation 39 as shown in FIG. 2. Beams ejected from the light source for fixation 39 pass the beam splitter 31 via the optical path 35, and transmit in a direction of the eye to be examined 40, so that the eye to be examined 40 can perceive the beams. At such a time, an image of the eye to be examined 40 enters the CCD camera 37 through the beam splitter 31 and the imaging lens 36 in the lower hand in the figure along the optical path 35, and the image processing portion 42 obtains an eye image IM.

Figure 3:
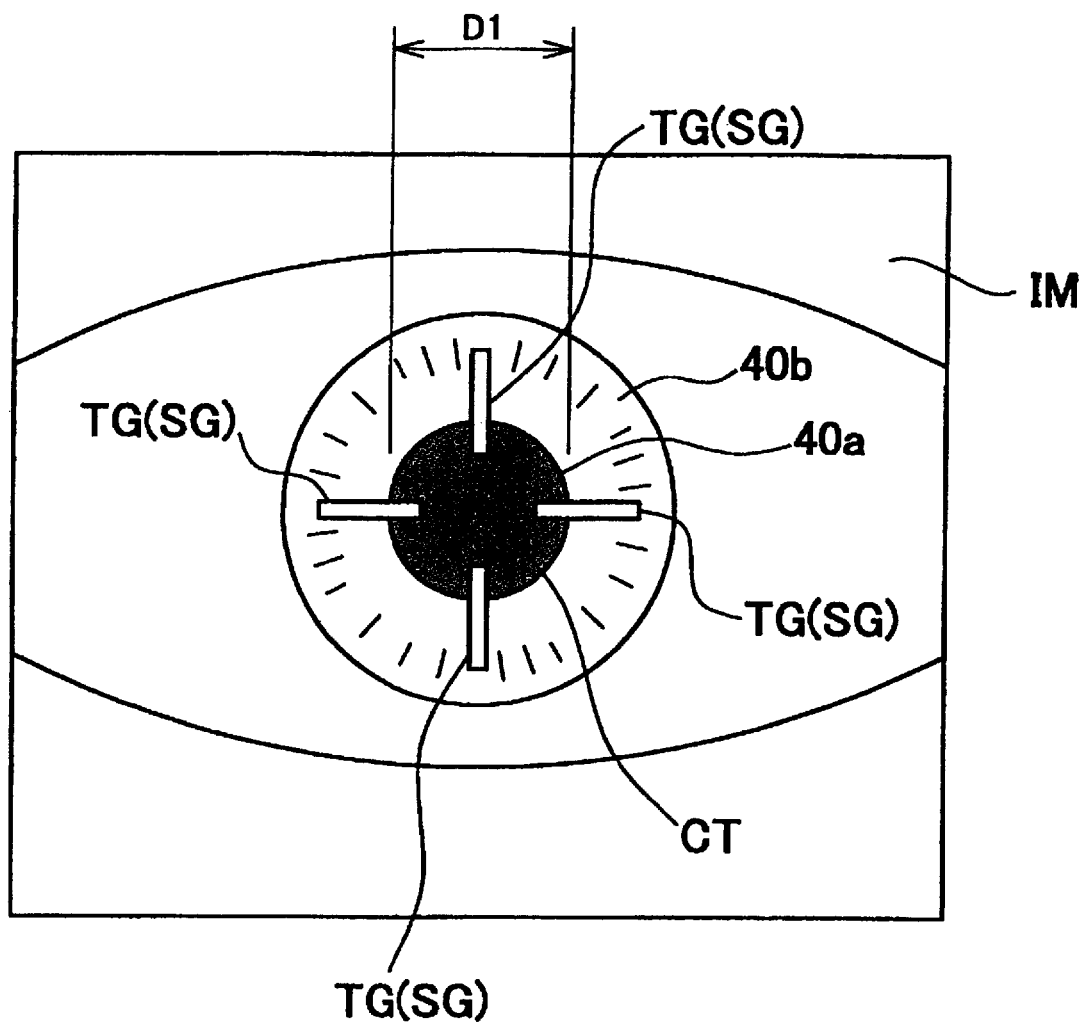
FIG. 3 is a view showing an example of an eye to be examined which is obtained by measurement on the pupil diameter.

At the same time, the lamp 34 is turned on so as to project an image of a stimulus TG which is located at the aperture 33 on the CCD camera 37 through the aperture 33, the lens 32, the beam splitter 31 and the imaging lens 36. Then, the eye image IM which is obtained by the CCD camera 37 is an image wherein the stimulus TG and the eye to be examined 40 are superimposed on each other, as shown in FIG. 3. The stimulus TG is located on the aperture 33 in advance so as to be a center of the image (screen) which is obtained by the CCD camera 37. And, the stimulus TG is comprised of four bar-shaped segments SG which are radially located at 90 degree intervals, for example, as shown in FIG. 3, and a central position CT which is a intersection among extension lines of these four segments SG corresponds to the central position of the dome 18. The segment may be photographed into the CCD camera 37 with an electronic photographic method in place of the above-mentioned optical photographic method.

In the above-mentioned state, the examiner moves the position of the eye to be examined 40 in up/down direction in FIG. 2 and in a direction orthogonal to a paper of FIG. 2 by adjusting the chin stand (not shown) so that a center of a pupil 40a (black spot portion in the figure) of the eye image IM which is captured by the CCD camera 37 is positioned at the central position CT which is the intersection among the extension lines of the four segments SG of the stimulus TG.

After positioning the center of the pupil 40a of the eye image IM at the central position CT which is the intersection among the extension lines of the four segments SG of the stimulus TG, the examiner instructs the pupil diameter computing portion 43 to compute a pupil diameter D1 of the eye to be examined 40 through the CPU 21 by operating the touch panel 29. The pupil 40a portion is perceived on the eye image IM in such a state that it is rather black in comparison with a peripheral iris portion 40b and its brightness is low. Therefore, the pupil diameter D1 can be easily computed by an image processing with a well known method.

After computing and measuring the pupil diameter D1 of the eye to be examined 40, the CPU 21 computes a shape proportion of the pupil diameter D1 of the eye to be examined 40 at the time of measurement to a standard pupil diameter DS as a shape parameter proportion according to a predetermined measurement program. That is, the CPU 21 computes a pupil area S1 of the eye to be examined 40 and an area proportion n of the pupil area S1 of the eye to be examined 40 to a standard pupil area SS of the standard pupil diameter DS which is stored in the memory 30 in advance is computed by an equation (1).

$$n = S1/SS \quad (1)$$

The standard pupil area SS is an average pupil area which has been obtained from actually measured data on the pupil diameters D1 of the eyes to be examined 40 of many examinees, and has been statistically measured in advance and is stored in the memory 30.

Subsequently, the CPU 21 drives the lamp 2 so as to drive the lamp 2 at a predetermined output read out of the memory 30. The lamp 2 is driven at a predetermined brightness according to drive output, and light energy corresponding to the brightness is radiated for the eye to be examined 40 from the lamp 2.

That is, the CPU 21 gradually changes the brightness (stimulus value) of the lamp 2 in one or more kinds of different strength under predetermined background light and measures a sensitivity SN of the eye to be examined 40 so as to correspond to the brightness of the lamp 2 on the basis of a response from the examinee. When actuating the perimeter in such a state that an examinee fixates a fixation point inside the visual field dome 18, the CPU 21 displays the stimuli 19 at various positions of the visual field dome 18 through the stimulus projecting mechanism 5 in order. The examinee operates the response switch 17 if he (she) perceives the stimulus 19, and does not operate the response switch 17 if not. But, the visual field of the examinee and sensitivity SN of the eye to be examined 40 at such a display position can be measured on the basis of the display position of the stimulus 19.

If the stimulus having a predetermined brightness (stimulus value) is presented and no response is received from the examinee, the brightness of the stimulus to be displayed is raised in such a state that the display position of the stimulus remains as it is, and the examiner waits a response from the examinee again. In a case of the perimeter in which three steps of stimuli can be displayed in connection with the brightness of the stimulus to be displayed, the sensitivity SN of the examinee in each measurement point can be classified into the following four steps. That is, (1) Step A wherein the darkest stimulus (such as brightness K1 of the lamp 2) is firstly presented, and thereafter, a response "perceived" is received. In such a case, a value of the sensitivity SN of the eye to be examined 40 in the measurement point is K1, for example.

(2) Step B wherein no response of (1) is received, and a rather brighter stimulus 19 (brightness K2 of the lamp >K1) is presented and a response "perceived" is received from the examinee. In such a case, a value of the sensitivity SN of the eye to be examined 40 in such a measurement point is K2, for example.

(3) Step C wherein no response of (2) is received, and further brighter stimulus (brightness K3 of the lamp 2>K2, for example) is presented and a response "perceived" is received from the examinee. In such a case, a value of the sensitivity SN of the eye to be examined 40 in such a measurement point is K3, for example.

(4) Step D wherein the examinee does not perceive any stimulus and no response in (1), (2) and (3) is received. In such a case, a value of the sensitivity SN of the eye to be examined 40 in such a measurement point is zero (0), for example.

By thus setting the sensitivity SN of the eye to be examined 40 in each measurement point into four steps from the response state of the eye to be examined 40, a diagram of sensitivity distribution which is comprised of steps A through D can be prepared for the eye to be examined 40, or a diagram of sensitivity distribution for storing the values of the sensitivity SN at the time of measurement in respective steps, K1 to K3 and zero (0) so as to correspond to respective measurement points can be prepared.

When the lamp 2 is driven at a predetermined output (stimulus value) under the background light by the lamp 16, the background light and the stimulus light from the lamp 2 pass the eye to be examined 40 having pupil diameter D1 and are radiated on a retina of the eye to be examined 40. In such a state, the background light and the stimulus light pass the pupil 40a of the eye to be examined 40, and their light energy is reduced by the area rate n of the standard pupil area SS of the standard pupil diameter DS. When the response from the eye to be examined 40 is obtained and measured in order to obtain the sensitivity SN of the eye to be examined 40 in the above-mentioned state, a response state is changed due to the pupil diameter D1 which was changed with respect to the standard pupil diameter DS and a virtual sensitivity SN which is different from an original sensitivity on the basis of a reaction to a stimulus value is obtained from the response of the eye to be examined under the background light and the stimulus light which were decreased due to the area rate n although the response of the eye to be examined 40 to the stimulus light having a predetermined stimulus value under a predetermined background light is to be originally obtained.

Then, the CPU 21 executes a procedure of correcting the obtained virtual sensitivity SN of the eye to be examined 40 at the time of measurement of the sensitivity SN of the eye to be examined 40 of each measurement point.

As shown in FIG. 4, the memory 30 stores a normal sensitivity distribution by age with respect to the standard pupil diameter DS which is set at each measurement point of the visual dome 18 so as to correspond to the age of the examinee and the p value which are shown in the examinee measurement information PI. A concrete value SNX of the sensitivity SN of the eye to be examined 40 is stored in each section ". . ." in a normal sensitivity distribution table TBL1 as shown in FIG. 4, but the value is not shown in the figure. The normal sensitivity distribution by age with respect to the standard pupil diameter DS is not always displayed as the table as shown in the figure, but may be displayed with a proper function or an algorithm.

The p value in FIG. 4 is a value which is statistically computed from perimetry database of normal healthy eyes. For example, "P value 5 percent" means that "if the examinees are normal persons, 95 percent (100−p value) of examinees can perceive the brightness of the stimulus at the position where the stimulus is indicated". The sensitivity SN of the eye to be examined 40 at the time when the p value is 5 percent changes due to ages or the position of the stimulus to be indicated, and the examinees who can perceive the stimulus are always included in 95 percent of all examinees. In FIG. 4, by classifying measurement results into five steps of sensitivity bounds, (1) $p \geqq = 5\%$, (2) $2\% \leqq p < 5\%$, (3) $1\% \leqq p < 2\%$, (4) $0.5\% \leqq p < 1\%$ and (5) $p < 0.5\%$ on the basis of the brightness of the lamp 2 when the examinee responds (value of the sensitivity SNX of the eye to be examined 40, "the sensitivity value" hereinafter), it is possible to judge the sensitivity of the eye to be examined 40 in the measurement point in the five steps according to ages of the examinees. The sensitivity value SNX which is a pause of such sensitivity step can be optionally set according to an object of the test, and the number of sensitivity steps is optional.

At such a judgment, the CPU 21 computes the sensitivity value SNX to be applied in FIG. 4 on the basis of the area rate n of the standard pupil area SS of the standard pupil diameter DS which was computed and obtained at the time of measurement.

As shown in FIG. 5, for example, virtual sensitivities SNX of many examinees have been measured under predetermined background light while the pupil diameter D1 (the area rate n) is variously changed with the eye to be examined 40 which sensitivity value SNX in the standard pupil diameter DS is a known value, and the memory 30 stores database of volume of correction y which are necessary at the time when correcting the virtual sensitivity value SNX which was measured in some area rate (shape parameter rate) into the sensitivity value SNX in the standard pupil DS in the shape of functions, values or algorithm as a correction table y (correction volume database). Any volume of correction y is available as long as it relates to the shape parameter rate which shows a size of the pupil 40a of the eye to be examined 40 measured to the standard pupil diameter. Therefore, the volume of correction may be expressed so as to correspond to the area rate n, or so as to correspond to the rate of a length between the measured pupil diameter D1 and the standard pupil diameter DS.

In case of the correction table TBL2 of FIG. 5, database of the volume of correction y by ages of the examinees is stored as the correction table TBL2, but such database may not be prepared by age, and the same volume of correction y may be used for all ages. If the age of the examinee and the area rate n which is the shape parameter rate of the pupil 40a of the eye to be examined at the time of measurement to the standard pupil diameter DS are known, the volume of correction y to the virtual sensitivity value SNX is immediately computed.

Then, the CPU 21 corrects the virtual sensitivity value SNX of the eye to be examined which was obtained from a reaction of the examinee with the computed volume of correction y so as to convert the value into the sensitivity value SNX to the standard pupil diameter DS, and the converted sensitivity value SNX is applied to the normal sensitivity distribution table TBL1 and is classified into the corresponding sensitivity step.

In such a case, the virtual sensitivity value SNX of the eye to be examined 40 is measured such that light energy of the background light and the stimulus light is equally decreased due to the pupil 40a of the area rate n. However, a correct sensitivity step can be obtained even if the measurement is conducted in such a state that the pupil 40a of the eye to be examined contracts rather than the standard pupil diameter DS under a predetermined background light since the volume of correction y is obtained from the correction table TBL2 according to the area rate n and the measurement result is converted into one in the standard pupil diameter DS.

In such a way, the perimetry is conducted on the eye to be examined 40 with the perimeter 50 at each measurement point of the visual dome 18. But, such perimetry method is known method. Then, its detailed explanation is not described.

The above-mentioned embodiment refers to the case where the invention is applied to the perimeter 50 as the ophthalmic apparatus. However, the invention can be applied to any ophthalmic apparatus as long as the apparatus is for testing the reaction state of the eye to be examined to the stimulus light by emitting the stimulus light having a predetermined light energy under the background light having a predetermined strength. For example, the invention can be also applied to ophthalmic apparatuses for testing a function of a yellow spot of a retina, such as an ERG (electroretinograph), a VEP (visual evoked potential), and a VER (visual evoked response).

Figure 6:
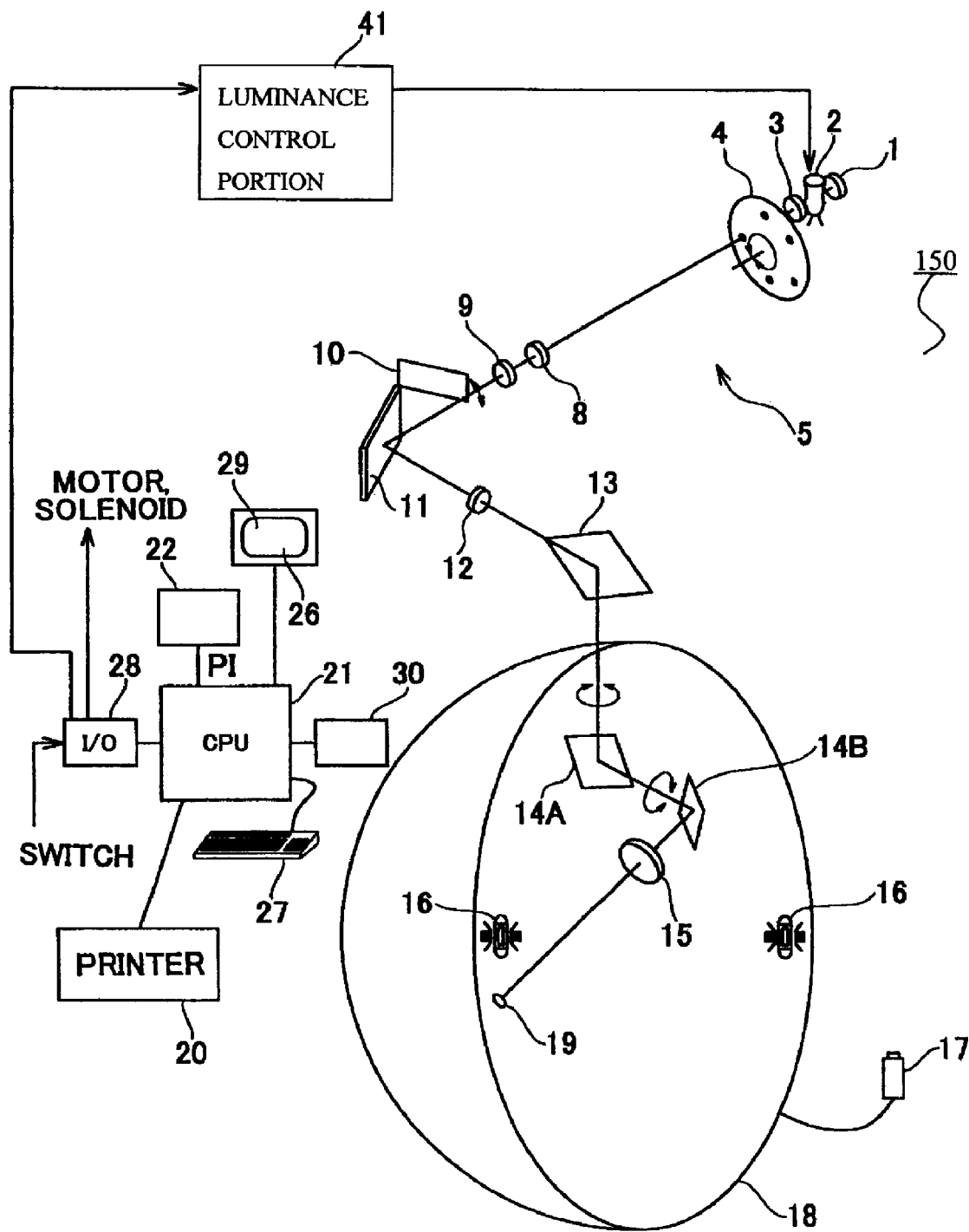
FIG. 6 is a view showing another example of the structure of the perimeter which is one of the ophthalmic apparatuses.

Subsequently, another embodiment of the invention is explained in connection with FIG. 6. The ophthalmic apparatus as shown in FIG. 6 has a structure almost similar to one as shown in FIG. 1, but a luminance control portion 41 connected with the lamp 2 is connected with the I/O port 28. Furthermore, the I/O port 28 is connected with the CCD camera 37 through the image processing portion 42 and the pupil diameter computing portion 43. In the ophthalmic apparatus as shown in FIG. 6 also, the structure as shown in FIG. 2 is used.

After computing and measuring the pupil diameter D1 of the eye to be examined 40, the CPU 21 computes the pupil area S1 of the eye to be examined 40 according to a predetermined measurement program, and area rate RT of the standard pupil area SS of the standard pupil diameter DS which is stored in the memory 30 in advance to the pupil area S1 of the eye to be examined 40 is computed with the following expression.

$$RT=SS/S1 \quad (2)$$

The memory 30 stores the standard output of the lamp 2 which corresponds to the standard stimulus value to the standard pupil area SS (standard pupil diameter DS). That is, the standard stimulus value is amount of light energy with which the luminance on the retina of the eye to be examined 40 is suitable for test when the light emitted from the lamp 2 passes the pupil 40a having the standard pupil area SS of the eye to be examined 40 and is radiated on the retina at the time of measurement on the eye to be examined 40 having the standard pupil area SS (standard pupil diameter DS). Then, the CPU 21 computes the correction output of the lamp 2 from the following expression (3) with the area rate RT.

Correction output of lamp 2=standard output of the lamp 2 corresponding to standard stimulus value $$* \text{ area rate RT} \quad (3)$$

And, the CPU 21 instructs the luminance control portion 41 to drive the lamp 2 at the computed correction output.

In such a case where a light which is outputted from an apparatus, such as a perimeter in the shape of a dome as shown in FIG. 6 and a full-field ERG (electroretinograph), and is emitted in the eye to be examined 40 is a diffused light reflected on the visual field dome 18, the area rate RT of the pupil area S1 of the eye to be examined 40 to the standard pupil area SS becomes a rate of pupil passing energy as it is. Then, the lamp 2 is controlled to be driven in such a manner that the output of the lamp 2 is made small since amount of light energy which is emitted into the eye to be examined 40 via the pupil 40a is increased when the pupil area S1 of the eye to be examined 40 becomes bigger than the standard pupil area SS, and the output of the lamp 2 is made large since amount of light energy which is emitted into the eye to be examined 40 via the pupil 40a is decreased when the pupil area S1 of the eye to be examined 40 becomes smaller than the standard pupil area SS. By doing so, a constant amount of light energy always passes the pupil 40a of the eye to be examined 40 so as to radiate on the retina regardless of the size of the pupil area S1 of the eye to be examined 40, and the luminance on the retina is controlled to be constant regardless of the pupil diameter D1 of the eye to be examined 40.

The standard pupil area SS is an average pupil area which has been obtained on the basis of data actually measured on the pupil diameters D1 of the eyes of many examinees, and was statistically measured in advance and stored in the memory 30. In addition, the standard output of the lamp 2 is the output of the lamp 2 (standard stimulus value) which is necessary to make the luminance on the retina of the eye to be examined 40 proper for text when emitting light on the eye to be examined 40 having the standard pupil area SS (standard pupil diameter DS).

Receiving the instruction from the CPU 21, the luminance control portion 41 drives the lamp 2 at the corrected output which was computed, and light energy having a strength according to the pupil diameter D1 (pupil area S1) of the eye to be examined 40, that is, having the corrected stimulus value is radiated, and the stimulus 19 is presented on the visual field dome 18 by the light energy having such corrected stimulus value. Then, constant volume of light energy is radiated on the retina of the eye to be examined 40 irrespective of the pupil area S1, and the luminance on the retina becomes a constant luminance proper for the test in spite of the pupil diameter D1 of the eye to be examined 40.

In case where light is successively emitted, it is desirable for the examinee to use mydriatic for maintaining the pupil diameter D1 in a stable state such that the pupil diameter D1 of the eye to be examined 40 is not changed due to a change of output of the lamp 2.

The quantity of light energy which passes the pupil 40a of the eye to be examined 40, that is, the luminance on the retina can be thus maintained stable regardless of its pupil diameter D1 (pupil area S1) by driving the lamp 2 at an output according to the pupil diameter D1 of the eye to be examined 40, and the response of the eye to be examined to predetermined amount of light energy can be correctly measured. In other words, perimetry is possible in such a state the luminance on the retina of the eye to be examined 40 is the same as one in case of the eye to be examined 40 having the standard pupil area SS in a perimeter 150 of FIG. 6.

In such a way, the perimetry is conducted on the eye to be examined 40 with the perimeter 150 in such a state that the luminance of the lamp 2 was corrected into a predetermined output. However, the perimetry method is well-known method. Then, its detailed explanation is not described.

The above-mentioned embodiment refers to such a case where the invention is applied to the perimeter 150 as the ophthalmic apparatus. However, the above-mentioned embodiment can be applied to any ophthalmic apparatus as long as in such an ophthalmic apparatus, it is necessary to make the luminance on the retina of the eye to be examined constant regardless of the size of the pupil diameter D1 of the eye to be examined 40. For instance, the invention can be applied to ophthalmic apparatuses for testing a function of a yellow spot of a retina, such as an ERG (electroretinograph), a VEP (visual evoked potential), and a VER (visual evoked response).

In the structure of the above-mentioned embodiment, the standard pupil area SS and the standard output of the lamp 2 corresponding to the standard pupil area SS are stored in the memory 30, and the standard output of the lamp is corrected according to the pupil area S1 (the pupil diameter D1) of the eye to be examined 40. However, the standard pupil area SS and the standard output of the lamp 2 are not always be necessary. That is, in another structure, the output of the lamp 2 may be computed so as to set the luminance on the retina of the eye to be examined 40 which is proper for test according to the size of the pupil area S1 of the eye to be examined 40, provided that such a luminance is properly set by an examiner through the touch panel 29 or the keyboard 27, and is stored in a memory in advance.

In other words, the invention may be constructed in such a manner the ophthalmic apparatus capable of radiating light energy from a lamp on a retina of an eye to be examined as a stimulus has (1) pupil diameter measuring means for measuring a pupil diameter of the eye to be examined, (2) pupil area computing means for computing a pupil area on the basis of the computed pupil diameter, (3) lamp output determining means for determining the output of the lamp such that the luminance on the retina of the eye to be examined becomes a predetermined luminance suitable for test on the basis of the computed pupil area, and (4) lamp control means for driving and controlling the lamp at the determined lamp output.

According to such a structure, the lamp output determining means determines the output of the lamp on the basis of the computed pupil area such that the luminance on the retina of the eye to be examined can become a predetermined luminance suitable for test, and the lamp control means drives and controls the lamp at the lamp output which was determined. Therefore, the luminance on the retina of the eye to be examined can be made a predetermined luminance which is suitable for test regardless of the pupil diameter by controlling to always constantly pass energy into the pupil, and a correct measurement result can be obtained thereby.

In addition, in the invention, the lamp output determining means has (1) memory means for storing in advance an average pupil area of eyes of many examinees as a standard pupil area, (2) memory means for storing in advance the output of the lamp which is necessary for making the luminance on the retina of the eye having the standard pupil area suitable for test as a standard output, (3) area rate computing means for comparing the computed pupil area of the eye to be examined and the standard pupil area and obtaining the area rate of both, and (4) the lamp output correcting means for computing and determining the output of the lamp which is necessary for making the luminance on the retina of the eye to be examined as a correction output on the basis of the obtained area rate and the standard output, and the lamp control means controls to drive the lamp at the correction output.

According to such an invention, the standard output of the lamp with respect to the standard pupil area is stored in advance and the output of the lamp is corrected so as to drive the lamp on the basis of the area rate between the pupil area of the eye to be examined and the standard pupil area, so that the luminance on the retina of the eye to be examined can be easily set on the luminance corresponding to the standard pupil area which is determined in advance.

Preferably, the standard pupil area and the standard output in the memory are stored as database by ages, sexes, visual grades of the examinees, and corresponding standard pupil area and standard output are read out of the memory according to ages, sexes, visual grades of the examinees so as to use.

The invention may be structured with the perimeter as the ophthalmic apparatus.

The invention may be structured with an ERG (elctroretinograph) as the ophthalmic apparatus.

INDUSTRIAL APPLICABILITY

The invention can be utilized as a perimeter which is one of ophthalmic apparatus.

The invention claimed is

1. An ophthalmic apparatus for computing a sensitivity value of an eye to be examined in a measurement point in such a manner that a stimulus light from a lamp having one, two or more different kinds of strength, is emitted on a retina of said eye to be examined from a predetermined said measurement point as a stimulus under a predetermined background light, and a response of an examinee to said stimulus light is obtained, comprising:
    a first memory for storing sensitivity database wherein a sensitivity of said eye to be examined in said measurement point which corresponds to said sensitivity value which is obtained with said eye to be examined having a standard pupil diameter when said stimulus light having one, two or more different kinds of strength is used as said stimulus under said predetermined background light is shown in two or more sensitivity steps;
    a second memory for storing volume of correction which is necessary for correcting a virtual sensitivity value which was measured with said pupil diameter of some shape parameter rate into a sensitivity value in a standard pupil diameter as a correction database after said virtual sensitivity value which is obtained when measuring said eye to be machined which sensitivity value in said standard pupil diameter is known, variously changing said pupil diameter under said predetermined background light is measured for many examinees in advance;
    a pupil diameter measuring unit for measuring a pupil diameter of said eye to be examined;
    a shape parameter rate computing unit for computing a shape parameter rate of said measured pupil diameter to said standard pupil diameter;
    a correction volume database for storing correction data on multiple shape parameter rates;

a correction volume computing unit for computing volume of correction by referring to said correction volume database and said shape parameter rate of said eye to be examined, wherein said volume correction is for correcting said virtual sensitivity value into said sensitivity value in a standard pupil diameter; and a sensitivity step judging unit for judging said sensitivity step of said eye to be examined in such a manner that said virtual sensitivity value which was obtained by a measurement of said eye to be examined is corrected into said sensitivity value in said standard pupil diameter by said computed volume of correction, and said corrected sensitivity value in said standard pupil diameter is referred to said sensitivity database.

2. The ophthalmic apparatus according to claim 1, wherein said ophthalmic apparatus is a perimeter.

3. The ophthalmic apparatus according to claim 1, wherein said ophthalmic apparatus is an ERG (Electroretinograph).

* * * * *